United States Patent
Meyer et al.

(10) Patent No.: US 6,469,787 B1
(45) Date of Patent: Oct. 22, 2002

(54) DYNAMIC LIGHT SCATTERING HOMODYNE PROBE

(75) Inventors: William V. Meyer, Lakewood, OH (US); David S. Cannell, Santa Barbara, CA (US); Anthony E. Smart, Costa Mesa, CA (US)

(73) Assignees: Ohio Aerospace Institute, Cleveland, OH (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/825,117

(22) Filed: Apr. 3, 2001

(51) Int. Cl.[7] .................. G01N 21/00; G01N 15/02; G01P 3/36; G01C 3/08
(52) U.S. Cl. .................. 356/342; 356/336; 356/28; 356/4.01
(58) Field of Search .................. 356/4.01, 28.5, 356/335, 343, 5.06, 5.09, 5.15; 385/9

(56) References Cited

U.S. PATENT DOCUMENTS

| | | | |
|---|---|---|---|
| 4,109,647 A | 8/1978 | Stern et al. | 128/2.05 |
| 4,171,159 A | 10/1979 | White | 356/349 |
| 4,692,023 A * | 9/1987 | Ohtomo et al. | 356/5 |
| 4,818,071 A | 4/1989 | Dyott | 356/28.5 |
| 4,975,237 A | 12/1990 | Brown | 356/338 |
| 4,977,620 A | 12/1990 | Smith et al. | 455/619 |
| 5,012,118 A * | 4/1991 | Preikschat et al. | 250/574 |
| 5,094,532 A | 3/1992 | Trainer et al. | 356/336 |
| 5,155,549 A | 10/1992 | Dhadwal | 356/336 |
| 5,231,463 A * | 7/1993 | Shambaugh | 356/336 |
| 5,268,739 A | 12/1993 | Martinelli et al. | 356/349 |
| 5,294,806 A | 3/1994 | Batchelder et al. | 250/574 |
| 5,343,290 A * | 8/1994 | Batchelder et al. | 356/349 |
| 5,398,130 A * | 3/1995 | Redman | 359/155 |
| 5,414,509 A | 5/1995 | Veligdan | 356/349 |
| 5,491,552 A | 2/1996 | Knuttel | 356/360 |
| 5,534,993 A * | 7/1996 | Ball et al. | 356/5.09 |
| 5,847,816 A | 12/1998 | Zediker et al. | 356/5.09 |
| 5,956,139 A | 9/1999 | Meyer et al. | 356/338 |
| 6,100,976 A * | 8/2000 | Ackerson | 356/336 |
| 6,181,430 B1 | 1/2001 | Meyer et al. | 356/495 |
| 6,332,093 B1 * | 12/2001 | Painchaud et al. | 600/476 |

OTHER PUBLICATIONS

W.V. Meyers, D.S. Cannell, R.G.W. Brown, J.A. Lock and T.W. Taylor, "Laser Light Scattering Multiple Scattering Suppression with Cross–Correlation, and Flare Rejection with Fiber Optic Homodyning", Paper AIAA–99–0962, 37th AIAA Aerospace Science Meeting and Exhibit, Reno, NV (Jan. 11–14, 1999), pp. 1–8.

Benjamin Chu, "Laser Light Scattering", Academic Press, NY, 1974, pp. 82–107.

* cited by examiner

Primary Examiner—Thomas H. Tarcza
Assistant Examiner—Brian Andrea
(74) Attorney, Agent, or Firm—Pearne & Gordon LLP

(57) ABSTRACT

An optical probe for analyzing a sample illuminated by a laser includes an input optical fiber operably connectable to the laser where the input optical fiber has an entrance end and an exit end. The probe also includes a first beam splitter where the first beam splitter is adapted to transmit an alignment portion of a light beam from the input fiber exit end and to reflect a homodyning portion of the light beam from the input fiber. The probe also includes a lens between the input fiber exit end and the first beam splitter and a first and a second output optical fiber, each having an entrance end and an exit end, each exit end being operably connectable to respective optical detectors. The probe also includes a second beam splitter which is adapted to reflect at least a portion of the reflected homodyning portion into the output fiber entrance ends and to transmit light from the laser scattered by the sample into the entrance ends.

15 Claims, 2 Drawing Sheets

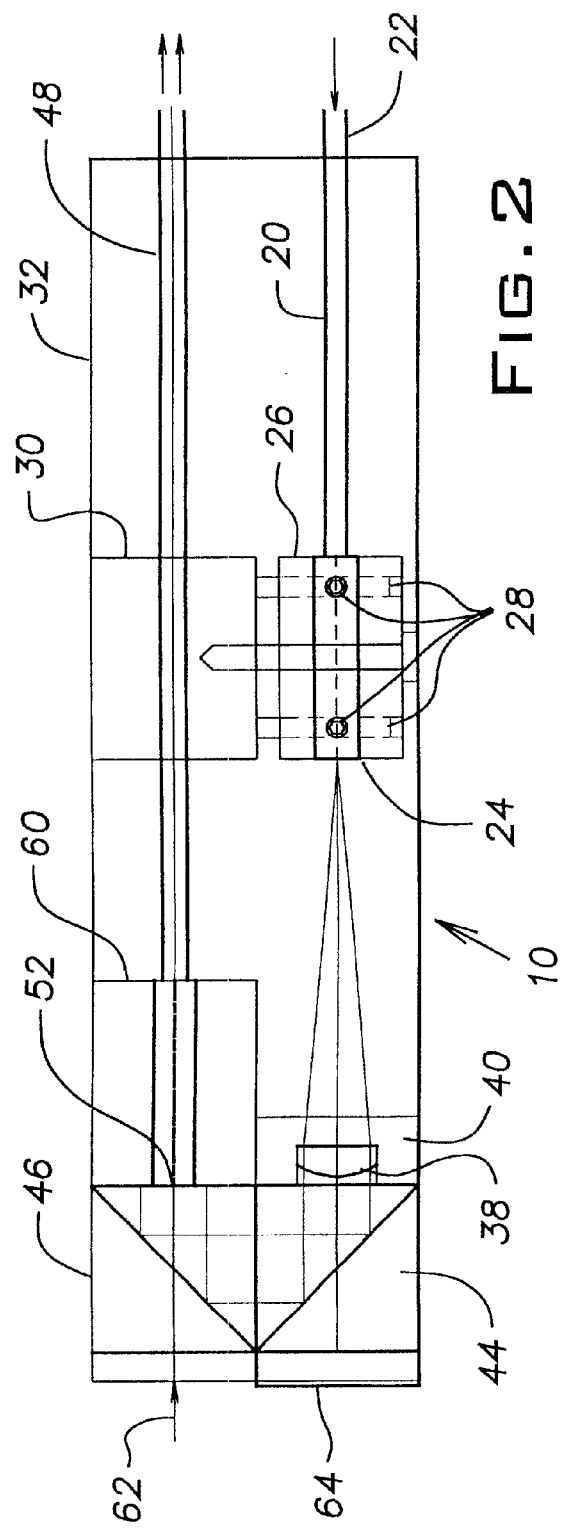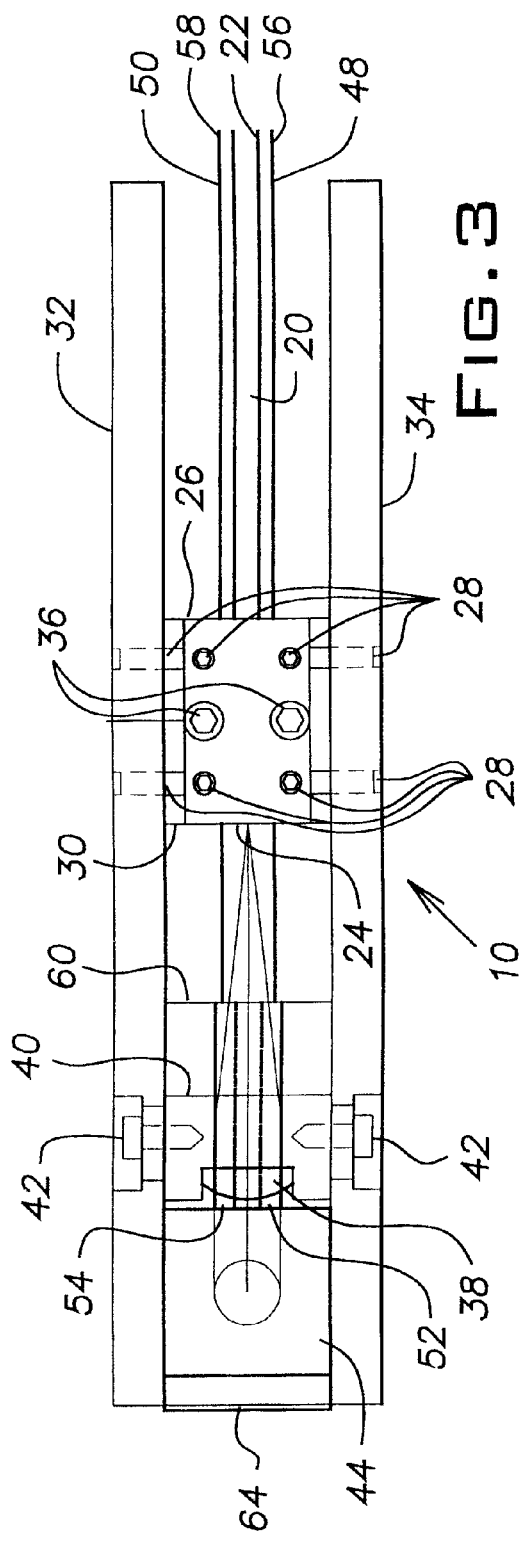

DYNAMIC LIGHT SCATTERING HOMODYNE PROBE

The United States Government has rights in this invention pursuant to NASA Contract No. NCC3-419.

BACKGROUND OF THE INVENTION

The present invention relates to the measurement of dynamic light scattering from particles in suspension and, in particular, to a homodyning probe for such measurements.

Dynamic light scattering (DLS) is a useful tool for measurement of the characteristics of particles in suspension. Optical scattering from a dilute monodisperse suspension is an ideal experimental configuration for characterizing a stable colloid. The performance of such measurements becomes more difficult in the following six regimes: where the sample tends to opacity, is not monodisperse, the particles are too small to scatter enough light, there is too little sample, the necessary geometry gives unwanted stray light (either coherent or incoherent flare), or the sample has non-Gaussian characteristics.

U.S. Pat. No. 5,956,139, which is incorporated herein by reference, provides significant improvements where the sample tends to opacity. Briefly stated, the patent teaches the use of cross-correlation between two spaced apart detectors to minimize the effects of multiple scattering.

U.S. Pat. No. 4,975,237, which is incorporated herein by reference, provides improvements in the other areas, i.e., the sample is not monodisperse, the particles are too small to scatter enough light, there is too little sample, the necessary geometry gives unwanted stray light (either coherent or incoherent flare), or the sample has non-Gaussian characteristics.

Substantial improvements are required in all of these regimes.

"Heterodyne amplification" to improve signal-to-noise ratio (SNR) has long been used in the radio art. Analogous techniques in the optical spectrum have been exploited similarly and, because the local oscillator is typically derived from the same coherent laser source as that which illuminates the probed sample, the operation has been commonly referred to as "homodyne" amplification. Square-law optical detectors measure intensity, the product of the incident field with its complex conjugate. The addition of a coherent optical field to the scattered field prior to detection permits the detected power to reflect the properties of the scattered electric field, rather than its customary intensity. The technique has been applied to DLS using autocorrelation, requiring only an arbitrary but stable phase for the local oscillator, and it is possible but technically challenging to build sufficiently stable apparatus, either on an optical table, or more recently using optical fibers as in U.S. Pat. No. 4,975,237. This technique does not improve the performance in the case where the sample tends to opacity. The incorporation of several techniques to address all six items simultaneously has been inhibited by the great difficulty of establishing a constant and stable phase relationship between the local oscillators mixed with the signal at each of the two detectors in U.S. Pat. No. 5,956,139, without which the measured correlation function tends to zero everywhere.

The present invention uses a novel and simple design for an optical probe which simultaneously overcomes past instabilities and makes possible the simultaneous use of homodyne detection and cross correlation incorporating all of the advantages included in the above-mentioned patents.

SUMMARY OF THE INVENTION

An optical probe for analyzing a sample illuminated by a laser includes an input optical fiber operably connectable to the laser where the input optical fiber has an entrance end and an exit end. The probe also includes a first beam splitter where the first beam splitter is adapted to transmit an alignment portion of a light beam from the input fiber exit end and to reflect a homodyning portion of the light beam from the input fiber. The probe also includes a lens between the input fiber exit end and the first beam splitter and a first and a second output optical fiber, each having an entrance end and an exit end, each exit end being operably connectable to respective optical detectors. The probe also includes a second beam splitter which is adapted to reflect at least a portion of the reflected homodyning portion into the output fiber entrance ends and to transmit light from the laser scattered by the sample into the entrance ends.

BRIEF DESCRIPTION OF THE DRAWINGS

FIG. 2 is a top plan view of a probe according to the invention.

FIG. 3 is a side elevation view of a probe according to the invention.

DESCRIPTION OF THE EMBODIMENTS

Figure 1:
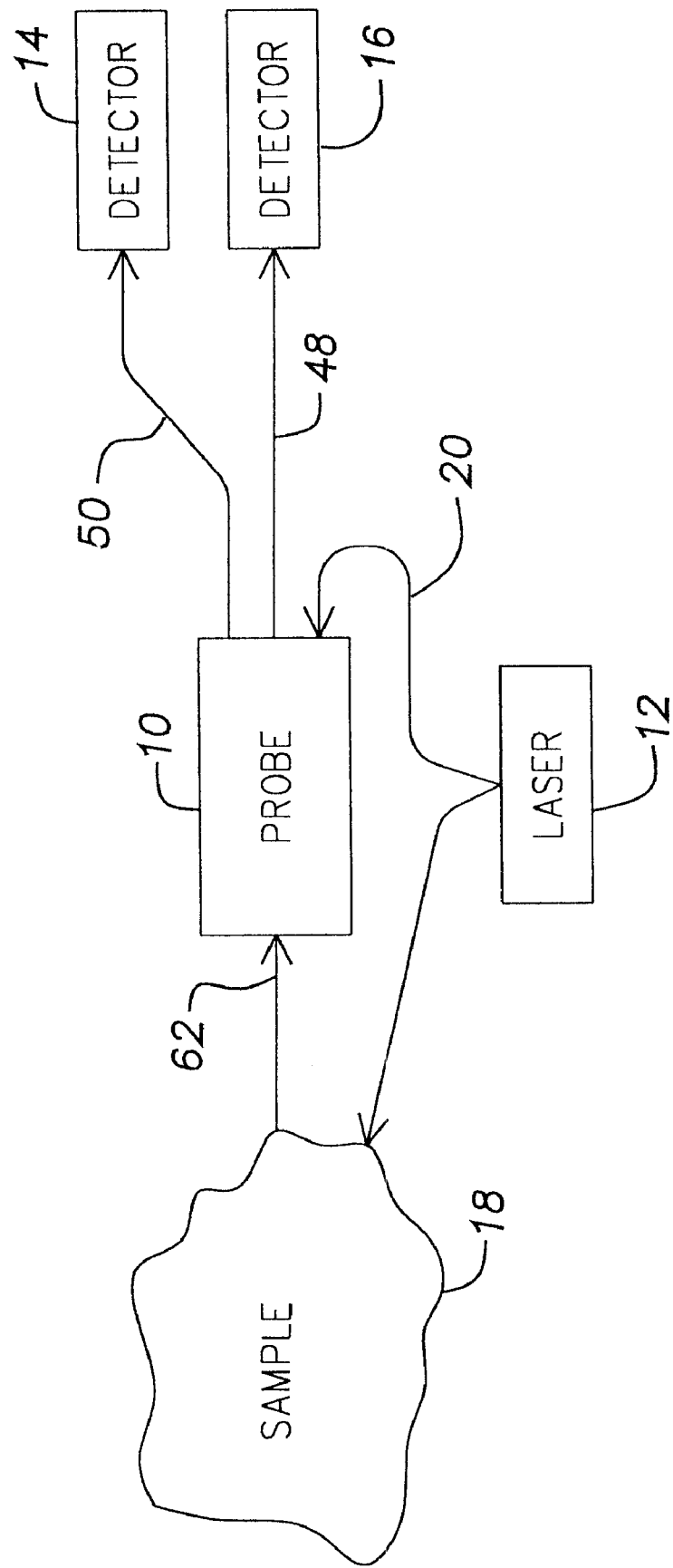
FIG. 1 is a block diagram of a dynamic light scattering system according to the invention.

Referring to FIG. 1, a dynamic light scattering measurement (DLS) system includes a probe 10, a laser 12, optical detectors 14, 16 and the sample 18 to be investigated. The laser 12 illuminates the sample 18 and supplies a portion of its output directly to the probe 10. The probe 10 receives scattered light from the sample 18 and, in combination with the light directly from the laser 12, provides light to each of the optical detectors 14, 16. The measurement output of the detectors 14, 16 are used to determine characteristics of the sample 18.

Referring to FIGS. 2 and 3, the probe 10 includes an input fiber 20 with an entrance end 22 and an exit end 24. The input fiber 20 is held in place by an adjustment block 26 having, for example, two degrees of freedom in the pointing direction and one degree of longitudinal translation. The adjustment block 26 may be adjusted with the adjustment screws 28. The adjustment block 26 is adjustably attached to the block 30 which is attached to aluminum side plates 32, 34 (side plate 34 is removed for clarity in FIG. 2). A pair of locking screws 36 are used to lock the adjustment block 26 to the block 30.

A lens 38 in a holder 40 (e.g., plano convex lens, 25.4 mm focal length, 6.3 mm diameter, Melles Griot 01LPX037) is mounted to the plates 32, 34 with one degree of freedom in the axial direction. The screws 42 allow the lens 38 and the holder 40 to be moved axially. The lens 38 is in line with the exit end 24 of the input fiber 20.

A beam splitting cube 44 having about 50 percent transmission at 800 nm is attached to the side plates 32, 34. Light from the exit end 24 of the input fiber 20 is partially transmitted through the cube 44 and partially reflected to another beam splitting cube 46 having about 50 percent transmission at 800 nm. The cube 46 is also attached to the side plates 32, 34. The light reflected from the cube 44 is partially reflected by the cube 46 (or vice versa). The cubes 44, 46 may have, for example, 10 mm sides, such as Melles Griot 03BSD044, 03BSL053, 03BSL063 or equivalents. The cubes 44, 46 may be, for example, located contiguously or spaced adjacently apart.

A pair of output fibers 48, 50 each having respective entrance ends 52, 54 and exit ends 56, 58 are mounted in the probe 10 with a support block 60 attached to the side plates 32, 34. The entrance ends 52, 54 of the output fibers 48, 50, respectively, are mounted (e.g., glued) with a fixed core separation (e.g., 2.5 mm). Scattered light 62 from the sample 18 enters the entrance ends 52, 54 along with any light from the exit end 24 of the input fiber 20.

The fibers 20, 48, 50 may be for example, single mode optical fibers having step index, bow tie strain birefringence or other core and cladding designs to assure that only a single mode is supported. It may also be advantageous to use fibers that preserve polarization.

An opaque shield 64 is mounted in front of the cube 44 during the operation of the probe 10. It may be, for example, be mounted to an unshown cover for the probe 10 thereby exposing the distal face of the cube 44 when the cover is removed allowing light from the input fiber 20 to exit the probe 10, but blocking transmission of the light from the input fiber 20 when the cover is installed.

Alignment of the probe 10 is accomplished by illuminating the entrance end 22 of the fiber 20 with the laser 12 (or other suitable laser) while the shield 64 is removed. The portion (e.g., 50 percent) of the light from the laser 12 that is transmitted through the cube 44, the "alignment portion", is then collimated by adjusting the axial position of the lens 38.

The portion of the light from the laser 12 that is reflected to the cube 44 and in turn towards the entrance ends 52, 54, the "homodyning portion", is then centered about the entrance ends 52, 54. This may be accomplished by adjusting the screws 28.

The exit ends 56, 58 are then illuminated with the laser 12 (or other suitable laser). A set of interference fringes appear at the exit end 24 in the exit plane. The screws 28 are then adjusted so that the exit end 24 lies on an interference fringe peak. It should be noted that it would also be possible to provide adjustment mechanisms for the entrance ends 52, 54 instead of, or in addition to, the adjustment block 26. The entrance ends 52, 54 and the exit end 24 are translated with respect to each other.

Alignment optimization may be verified by measuring uniformity of intensity transmitted from the output fibers with the input fiber supplying optical power, and conversely by optimizing the power transmitted by the input fiber with the output fibers illuminated by the laser. Very small iterations with the adjustment screws 32 can be performed until the two conditions are matched.

Once the probe 10 is aligned, subsequent changes in homodyne launch, detectors, even possible change of wavelength (since the lens 38 is achromatic), will not impair the capability to place the probe anywhere in the equivalent speckle pattern of a scattering medium and obtain good measurements even though the sample tends to opacity, is not monodisperse, the particles are too small to scatter enough light, there is too little sample, the necessary geometry gives unwanted stray light (either coherent or incoherent flare), or the sample has non-Gaussian characteristics.

Outputs from the optical detectors 14, 16 are fed to unshown analog or digital processing devices which in combination with either permitting or blocking the light input to the fiber 20 allow the probe 10 to operate in several modes: one detector, no homodyning gives conventional single point autocorrelation; two detectors give cross correlation of two closely spaced detectors; one detector and homodyning gives autocorrelation of single point detection with homodyne gain; and two detectors and homodyning gives cross correlation of detectors with cophasal local oscillators of the same intensity.

The addition of a local oscillator makes possible the measurement of particles in a sample that may be too small for conventional DLS. Although detection is still limited by shot noise in the signal, the consequences of other seriously detrimental sources of noise, such as stray light, are significantly mitigated. Even system noise from all other sources is rendered much less serious because we are now dealing with a relatively large detected signal, so large in fact that analog detection is now possible and significant further simplifications of the equipment are possible. Indeed since the typical ratio of additive homodyne power to that in the signal should be between about 10 and 1000 times the scattered signal, for example, at least 100, and as much higher as possible consistent with noise in the laser, continuing to use singlephoton detection may be detrimental in terms of pulse pile-up, and other introduced non-linearities. Any effects of afterpulsing, it will be noted, are already essentially eliminated by the use of cross correlation.

Using homodyne gain makes possible the measurement of much smaller particles, even where the amount of light scattered, from nearly transparent suspensions, for example, is extremely small. The simultaneous use of two cross correlated detectors allows good measurements from such low concentration of nanometer-size particles up to even quite turbid suspensions, should these occur or be of interest.

Stray light of different wavelength from that of the illuminating laser may of course be removed by a narrow band filter. Coherent stray light at the laser wavelength may not be so removed but may be overwhelmed by the addition of excess homodyne light. The advantages of similarly overwhelming coherent stray light are of a different order since this can substantially improve the retrieval of good information from what is essentially an ill-conditioned problem. There are several aspects to this improvement. The first may be seen by comparing the correlation function from square law detection of the signal scattered from the sample alone with that from the summation of the scattered field with a homodyne field. The measured decay rate of the correlogram is decreased by a factor of two when a dominant local oscillator is added. With coherent flare, the function is a combination of a variable and unknown ratio of decay rates differing by a factor of two. Even with a known monodispersion this can yield large and occasionally unexpected, or even undetected, errors. The addition of excess local oscillator moves the experiment into a region where the signal from light without heterodyne gain is negligible.

The second significant improvement is that with an excess local oscillator, the cross terms between components of a polydispersion or a number of discrete different sizes of particle are rendered insignificant, substantially improving the ability to extract useful measurements from the correlogram. Each decay rate is now simply found in terms of its individual homodyne multiplier, although the separation of several decay rates remains an ill-conditioned problem, particularly if they are closely spaced or of greatly different amplitudes. Such an approach ameliorates the errors associated even with a single exponential, where traditionally an imperfect model can yield an excellent fit while being in error by up to a factor of two.

The empirical avoidance of coherent flare has proved particularly challenging, and for small sample volumes very near impossible: however the addition of excess local oscillator reduces the significance of this parasitic effect by making it dominant in a known way. An additional advantage of reducing the significance of flare is the increased range of scattering angles that become available.

With conventional DLS, and where the absence of coherent flare may be independently assured, the measured correlation function is that of scattering intensity, whereas many of our desired inferences are based upon assumptions about the nature of the scattered electric field. In most experiments we assume Gaussian scattering statistics and invoke the Siegert relationship to justify inferences about the field properties from measurements of intensity properties. Complex colloids and other media do not necessarily have Gaussian statistics, rendering this assumption less secure. Intensity measurements using homodyne gain are essentially dependent upon the scattered field, since it is multiplied by a constant rather than squared at detection. This means that inferences need not necessarily be confined to the assumption of Gaussian statistics.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. An optical probe for analyzing a sample illuminated by a laser, said probe comprising:
   an input optical fiber operably connectable to said laser, said input optical fiber having an entrance end and an exit end;
   a first beam splitter, said first beam splitter being adapted to transmit an alignment portion of a light beam from said input fiber exit end and to reflect a homodyning portion of said light beam from said input fiber;
   a lens between said input fiber exit end and said first beam splitter;
   a first and a second output optical fiber, each having an entrance end and an exit end, each exit end being operably connectable to respective optical detectors; and
   a second beam splitter, said second beam splitter being adapted to reflect at least a portion of said reflected homodyning portion into said output fiber entrance ends and to transmit light from said laser scattered by said sample into said entrance ends.

2. A probe according to claim 1, wherein said first and second beam splitters are adjacent.

3. A probe according to claim 1, wherein said first and second beam splitters are contiguous.

4. A probe according to claim 1, wherein the power of said homodyning portion is between about 10 and about 1000 times the power of said light from said laser scattered by said sample into said entrance ends.

5. A method for aligning an optical probe for analyzing a sample illuminated by a laser, said method comprising:
   providing a probe having:
      an input optical fiber operably connectable to said laser, said input optical fiber having an entrance end and an exit end;
      a first beam splitter, said first beam splitter being adapted to transmit an alignment portion of a light beam from said input fiber exit end and to reflect a homodyning portion of said light beam from said input fiber;
      a lens between said input fiber exit end and said first beam splitter;
      a first and a second output optical fiber, each having an entrance end and an exit end, each exit end being operably connectable to respective optical detectors; and
      a second beam splitter, said second beam splitter being adapted to reflect at least a portion of said reflected homodyning portion into said output fiber entrance ends and to transmit light from said laser scattered by said sample into said entrance ends.
   illuminating said input fiber entrance end with said laser;
   using said lens to collimate said alignment portion;
   centering said homodyning portion on said output fiber entrance ends;
   illuminating said output fiber exit ends with said laser;
   observing an interference fringe at said input fiber exit end; and
   translating said output fiber entrance ends with respect to said input fiber exit end to produce an interference fringe peak at said input fiber exit end.

6. A probe according to claim 1, said lens being achromatic.

7. A probe according to claim 1, wherein said input optical fiber and said first and second output optical fibers are single mode optical fibers.

8. A probe according to claim 1, wherein each said respective optical detector detects a respective scattered light signal delivered thereto by said first and second output optical fibers respectively, said respective signals being cross-correlated.

9. A method according to claim 5, further comprising the steps of:
   illuminating a sample of interest with a laser; and
   directing scattered laser light from said sample to said respective optical detectors via said first and second output optical fibers respectively.

10. A method according to claim 9, wherein output signals from said respective optical detectors are cross-correlated.

11. A method according to claim 9, wherein said sample is not monodisperse.

12. A method according to claim 9, wherein said sample is non-Gaussian.

13. A method according to claim 9, wherein said sample is substantially opaque.

14. A method according to claim 9, wherein said sample is a turbid suspension.

15. A method according to claim 9, wherein said sample is a substantially transparent suspension having nanometer-size particles.

* * * * *